(12) United States Patent
Carney (10) Patent No.: US 9,675,503 B2
(45) Date of Patent: Jun. 13, 2017

(54) BODY FLUID TEST ARRANGEMENT FOR AN ABSORBENT ARTICLE

(71) Applicant: SCA Hygiene Products AB, Gothenburg (SE)

(72) Inventor: Joshua Carney, Gothenburg (SE)

(73) Assignee: SCA Hygiene Products AB, Gothenburg (SE)

( * ) Notice: Subject to any disclaimer, the term of this patent is extended or adjusted under 35 U.S.C. 154(b) by 55 days.

(21) Appl. No.: 14/652,582

(22) PCT Filed: Dec. 21, 2012

(86) PCT No.: PCT/SE2012/051496
§ 371 (c)(1),
(2) Date: Jun. 16, 2015

(87) PCT Pub. No.: WO2014/098695
PCT Pub. Date: Jun. 26, 2014

(65) Prior Publication Data
US 2015/0359689 A1 Dec. 17, 2015

(51) Int. Cl.
*A61F 13/42* (2006.01)
*A61F 13/84* (2006.01)
(Continued)

(52) U.S. Cl.
CPC .............. *A61F 13/84* (2013.01); *A61B 5/207* (2013.01); *A61B 5/6804* (2013.01);
(Continued)

(58) Field of Classification Search
CPC .............................................. A61F 2013/8473
See application file for complete search history.

(56) References Cited

U.S. PATENT DOCUMENTS 3,891,507 A * 6/1975 Breuer ................. G01N 33/523
422/537
3,918,433 A * 11/1975 Fuisz ................... A61B 10/007
600/573
(Continued)

FOREIGN PATENT DOCUMENTS

AU 2012397348 A1 7/2015
DE 198 37 678 A1 3/2000
(Continued)

OTHER PUBLICATIONS

Machine Translation of DE 2007005962U1, Swiss Medical Solution AG, Oct. 11, 2007.*
(Continued)

*Primary Examiner* — Paula L Craig
(74) *Attorney, Agent, or Firm* — Buchanan Ingersoll & Rooney PC (57) ABSTRACT

A body fluid test arrangement for an absorbent article includes a body fluid test device for receiving and examining voided body fluid. The body fluid test arrangement is configured to attach to a topsheet of the absorbent article. The body fluid test arrangement includes a fastening means for attachment to the topsheet of the absorbent article by a peelable connection between the body fluid test arrangement and the topsheet. The fastening means provides an attachment of the body fluid test arrangement having a peel strength from 0.05 to 1.65 (N×cm)/cm². An absorbent article including a body fluid test arrangement also is provided.

15 Claims, 3 Drawing Sheets

(51) Int. Cl.
  *A61B 5/20* (2006.01)
  *A61B 5/00* (2006.01)
  *A61B 10/00* (2006.01)
  *A61F 13/513* (2006.01)

(52) U.S. Cl.
  CPC ........ *A61B 10/007* (2013.01); *A61B 10/0038* (2013.01); *A61F 13/42* (2013.01); *A61F 13/513* (2013.01); *A61B 5/6808* (2013.01); *A61B 2010/0006* (2013.01); *A61F 2013/8473* (2013.01)

(56) References Cited

U.S. PATENT DOCUMENTS

| | | | | |
|---|---|---|---|---|
| 3,978,818 | A * | 9/1976 | Heldenbrand | A01K 1/0107 119/170 |
| 4,019,517 | A * | 4/1977 | Glassman | A61F 13/8405 604/359 |
| 4,072,150 | A * | 2/1978 | Glassman | A61F 13/493 604/372 |
| 4,136,699 | A * | 1/1979 | Collins | A61F 13/5611 428/355 BL |
| 4,197,849 | A * | 4/1980 | Bostick | A61F 5/4401 4/144.3 |
| 4,405,310 | A * | 9/1983 | Karami | A61F 13/474 604/383 |
| 4,576,597 | A * | 3/1986 | Hlaban | A61F 13/55145 604/385.21 |
| 4,700,714 | A * | 10/1987 | Fuisz | A61B 10/007 600/580 |
| 5,591,153 | A * | 1/1997 | Mattingly, III | A61F 13/15747 604/385.05 |
| 5,823,953 | A | 10/1998 | Roskin et al. | |
| 5,910,137 | A * | 6/1999 | Clark | A61F 13/505 604/385.04 |
| 6,025,071 | A * | 2/2000 | Cameron | C08L 53/025 428/355 BL |
| 6,280,427 | B1 * | 8/2001 | Maggiulli | A61F 13/505 604/385.01 |
| 6,981,951 | B1 | 1/2006 | Rahe | |
| 7,872,168 | B2 | 1/2011 | Sawyer et al. | |
| 9,072,807 | B2 | 7/2015 | Katsuragawa et al. | |
| 2001/0011167 | A1 | 8/2001 | Bouchard | A61B 10/0045 604/385.05 |
| 2001/0053876 | A1 * | 12/2001 | Torok | A61B 5/4294 600/361 |
| 2002/0143316 | A1 * | 10/2002 | Sherrod | A61F 13/505 604/385.101 |
| 2005/0124072 | A1 | 6/2005 | Boga et al. | |
| 2005/0215924 | A1 * | 9/2005 | Kao | A61B 10/0045 600/573 |
| 2006/0199897 | A1 * | 9/2006 | Karjala | A61L 15/58 524/543 |
| 2007/0287974 | A1 * | 12/2007 | Bonelli | A61F 13/58 604/385.03 |
| 2008/0269707 | A1 | 10/2008 | Song | |
| 2008/0274014 | A1 | 11/2008 | Jumonville et al. | |
| 2008/0274495 | A1 * | 11/2008 | Jumonville | A61B 10/007 435/30 |
| 2009/0209929 | A1 * | 8/2009 | Ito | A61F 13/474 604/359 |
| 2010/0191210 | A1 * | 7/2010 | Hayashi | A61F 13/47 604/385.23 |
| 2011/0065139 | A1 * | 3/2011 | Mullerad | C12Q 1/42 435/21 |
| 2011/0251575 | A1 * | 10/2011 | Kuroda | A61F 13/4704 604/380 |
| 2012/0109092 | A1 * | 5/2012 | Austin | A61F 13/505 604/385.03 |
| 2012/0157947 | A1 * | 6/2012 | Nhan | A61F 13/42 604/361 |
| 2013/0261409 | A1 * | 10/2013 | Pathak | A61B 5/0022 600/301 |
| 2013/0331666 | A1 * | 12/2013 | Miller | A61B 5/1405 600/309 |
| 2014/0039443 | A1 | 2/2014 | Nagai et al. | |
| 2015/0359689 | A1 | 12/2015 | Carney | |

FOREIGN PATENT DOCUMENTS

| | | |
|---|---|---|
| DE | 20 2007 005 962 U1 | 9/2007 |
| EP | 0 560 099 A2 | 9/1993 |
| EP | 1 150 609 B1 | 7/2005 |
| EP | 2934416 A1 | 10/2015 |
| JP | 2001-289845 A | 10/2001 |
| JP | 2002-17778 A | 1/2002 |
| JP | 2006-314361 A | 11/2006 |
| JP | 2007-509694 A | 4/2007 |
| WO | WO 97/49338 A1 | 12/1997 |
| WO | WO 00/45705 A1 | 8/2000 |
| WO | WO 00/57827 A1 | 10/2000 |
| WO | WO 03/009798 A2 | 2/2003 |
| WO | 2012/101934 A1 | 8/2012 |
| WO | 2012/105589 A1 | 8/2012 |
| WO | 2014/098695 A1 | 6/2014 |

OTHER PUBLICATIONS

Human translation of DE202007005962U1 to Swiss Medical Solution AG, Oct. 2007.*
Office Action (Examination Search Report) issued on Jun. 3, 2016, by the Canadian Intellectual Property Office in Canadian Patent Application No. 2,895,412 (4 pages).
International Search Report (PCT/ISA/210) mailed on Sep. 24, 2013, by the Swedish Patent Office as the International Searching Authority for International Application No. PCT/SE2012/051496.
Written Opinion (PCT/ISA/237) mailed on Sep. 24, 2013, by the Swedish Patent Office as the International Searching Authority for International Application No. PCT/SE2012/051496.
International Preliminary Report on Patentability (PCT/IPEA/409) dated May 11, 2015, by the Swedish Patent Office as the International Preliminary Examining Authority for International Application No. PCT/SE2012/051496.
Office Action (Notification of Reasons for Refusal) issued on Jul. 4, 2016, by the Japanese Patent Office in corresponding Japanese Patent Application No. 2015-549312, and an English Translation of the Office Action. (9 pages).
Office Action in corresponding Colombian Patent Application No. 15167292 (10 pages) dated Jan. 30, 2017.
Decision of Rejection issued in corresponding Japanese Patent Application No. 2015-549312, dated Feb. 27, 2017, with English Translation (7 pages).

* cited by examiner

BODY FLUID TEST ARRANGEMENT FOR AN ABSORBENT ARTICLE

TECHNICAL FIELD

The present disclosure relates to a body fluid test arrangement for an absorbent article such as an absorbent garment. The arrangement is meant to be attached to a topsheet of the absorbent article and arranged for receiving and examining voided body fluids such as urine. The disclosure also relates to an absorbent article comprising a body fluid test arrangement.

BACKGROUND

Body fluid detection devices are used for determining properties and/or constituents of body fluids such as urine excreted from a person. For example, a urine detection device is often placed inside a transparent urine collecting bag that is attached to the leg of a person from whom the urine is collected via a tube arrangement. Such a urine detection device may be provided with indicators for determining, for example, nitrite and leukocyte contents as well as electrolyte and pH values in the excreted urine. The indicators, to which urine is exposed, may be used to examine urine for developing and existing pathogen infections, which, for example, correspond to the pH, nitrite, leukocyte and electrolyte values in the urine. The indicators may for example react to constituents in the urine by a color change. A device of this type is disclosed in EP 0 560 099 A2.

EP 1150 609 B1 discloses a device of the mentioned type for receiving and controlling voided body fluids such as urine. Nevertheless, in many cases, it would be useful to arrange a urine detection device directly in an absorbent article such as a diaper for collecting voided urine and determining constituents of the urine voided.

DE 20 2007 005 962 U1 discloses a device for detecting uncontrolled voided urine for at least one property of the excreted urine. The device is arranged in layers placed on top of each other with a flat thin guidance nonwoven layer for receiving the excreted body fluid, in particular for holding urine and a flat thin adhesive nonwoven layer having approximately the same size as the guidance nonwoven. The adhesive nonwoven layer covers one side of the guidance nonwoven layer and is connected thereto. Furthermore, the adhesive nonwoven layer is on one side provided with an adhesive. The adhesive nonwoven layer also has a central opening being in flow communication with the guidance nonwoven layer.

In the region of the central opening, there is arranged test means in the form of a test card, which has an opening port for guiding the urine that has been absorbed by the guidance nonwoven layer into the test means via the central opening. The test means may be the urine detection device that is described in EP 1150609 B1.

The device disclosed in DE 20 2007 005 962 U1 is intended to be placed in a diaper or the like as an insert which is glued to a surface of an inner cover, i.e. topsheet, of the diaper by the means of the adhesive layer.

One problem with the arrangement disclosed in DE 20 2007 005 962 U1 is that the test means has to be removed after the urine has been collected in order to be able to determine the urine properties and/or contents. The removal of the insert arrangement may lead to the risk of disruption of the material of the topsheet, which may cause problems in determining the urine properties and/or contents as well hazardous risks to persons such as nursing staff in contact thereto due the exposure to body excretions, for example.

Although said prior art insert test device to some extent may alleviate the problems of properly placing and securing a test means such as urine detection device in an absorbent article such as a diaper, there is still a need for further improvements of test arrangements so as to provide an arrangement that is easy and safe to use and produce.

SUMMARY

In view of known test arrangements, it is an object to provide an improved body fluid test arrangement for placement in an absorbent article and attachment thereto, which provides a way of properly securing the arrangement in the absorbent article, while being easy and safe to use.

In one embodiment, a body fluid test arrangement for an absorbent article comprises a body fluid test device for receiving and examining voided body fluid, said body fluid test arrangement being configured to attach to a topsheet of the absorbent article, wherein said body fluid test arrangement comprises a fastening means for attachment to the topsheet of the absorbent article by a peelable connection between the body fluid test arrangement and the topsheet, wherein the fastening means provides an attachment of the body fluid test arrangement having a peel strength from 0.05 to 1.65 $(N \times cm)/cm^2$ as measured according to the peel test method as described herein.

In another embodiment, an absorbent article comprising a topsheet, a backsheet and an absorbent core enclosed between said topsheet and said backsheet, wherein the absorbent article further comprises a body fluid test arrangement described herein, wherein said body fluid test arrangement is releasably attached to the topsheet of the absorbent article.

According to one aspect, there is provided a body fluid test arrangement for an absorbent article, wherein the arrangement comprises a body fluid test device for receiving and examining voided body fluid. The arrangement is attachable to a topsheet of the absorbent article. Said arrangement comprises a fastening means for attachment to the topsheet of the absorbent article by a peelable connection between the arrangement and the topsheet. The fastening means provides an attachment of the arrangement having a peel strength of from about 0.05 to 1.65 $(N \times cm)/cm^2$ as measured according to the peel test method as described in the specification hereinbelow under the section relating to test methods and examples.

The term absorbent article refers to a product that is placed against the skin of the wearer to absorb and contain body exudates, like urine and faeces. The disclosure mainly refers to disposable absorbent articles, which are articles that are not intended to be laundered or otherwise restored or reused as an absorbent article after use. The absorbent article may be an incontinence pad, a sanitary pad or an absorbent garment such as a diaper and/or an incontinence guard that is intended be worn as a pant-type of absorbent article that may be in a belted or non-belted form for securing the garment around a wearer's waist as in known in the art.

The term a topsheet refers a sheet or the like that forms the inner cover of the absorbent article and in use is placed in direct contact with the skin of the wearer. The topsheet may comprise a fiber material such as a nonwoven material, e.g. spunbond, meltblown, carded, hydroentangled, wetlaid etc. Suitable fiber materials can be composed of natural fibers, such as wood pulp or cotton fibers, manmade fibers, such as polyester, polyethylene, polypropylene, viscose, nylon etc.

or from a mixture of natural and manmade fibers. The topsheet material may further be composed of tow fibers, which may be bonded to each other in a bonding pattern, as e.g. disclosed in EP-A-1 035 818. Further examples of topsheet materials are porous foams, apertured plastic films etc. The materials suited as topsheet materials should be soft and non-irritating to the skin and be readily penetrated by body fluid, e.g. urine. The topsheet may further be different in different parts of the absorbent article.

The body fluid test device is arranged for receiving and examining voided body fluid. Thus, it is intended for collecting discharged body fluids, such as urine, and determining properties related thereto and/or constituents therein. The arrangement may, for example, be used for detecting uncontrollably discharged urine.

The body fluid test device may also be arranged for testing urine for developing and existing pathogen infections, which, for example, correspond to pH, nitrite, leukocyte and electrolyte values in the urine. Thus, a urinary tract infection (UTI) may be determined using the test arrangement. Such a body fluid test device in the form of a test card is described in EP 1150609 B1 and DE 20 2007 005 962 U1, in which test card there is arranged color indicator strips for determining constituents such as nitrite and leukocyte, It will be appreciated by the person skilled in the art which types of reagents that are necessary for determining pH, leukocyte, nitrite and/or electrolyte contents, and thereby determining whether or not there exists a UTI. For example, the leukocyte content may be determined using indoxyl as an indicator reagent.

It will also be appreciated by the person skilled in the art that any other body fluid test devices such as a wetting indicator that is known in the art may also be used in the present body fluid test arrangement.

The peelable connection between the arrangement and the topsheet provides a releasable attachment of the arrangement to the topsheet.

By a releasable attachment as used herein is meant that an object may be attached to a surface and later on detached from that surface causing substantially no disruptions of the object and the surface. Furthermore, an object that has been peeled off may also be reattached to a surface again.

A body fluid test arrangement having a fastening means that provides said peel strength of from about 0.05 to 1.65 (N×cm)/cm$^2$) as measured in the peel test method described hereinbelow would provide releasable attachment to a topsheet.

By the body fluid test arrangement providing said peel strength, there is provided a possibility of releasably attaching the arrangement to the topsheet of an absorbent article such that a "proper" adhesion or attachment to the topsheet is achieved while the detachment of the insert from the topsheet should not cause any or little disruption of the topsheet, thereby being safe to use and with no hazardous risks involved in the detachment of the insert from the topsheet.

Said peel strength may be from about 0.05 to 1.4 (N×cm)/cm$^2$). For a secure attachment under the conditions during which the body fluid test arrangement is used in an absorbent article that is worn by a wearer from about, the peel strength may be about 0.08 (N×cm)/cm$^2$ or more, about 0.1 (N×cm)/cm$^2$ or more, about 0.15 (N×cm)/cm$^2$ or more, about 0.30 (N×cm)/cm$^2$ or more or about 0.5 (N×cm)/cm$^2$ or more. In order to safeguard a safe peelable removal of the body fluid test arrangement from the topsheet and minimize the possibility of disrupting the topsheet when the body fluid arrangement is peeled off from said topsheet, said peel strength may be about 1.4 (N×cm)/cm$^2$ or less, about 1.3 (N×cm)/cm$^2$ or less, about 1.0 (N×cm)/cm$^2$ or less, about 0.8 (N×cm)/cm$^2$ or less, about 0.5 (N×cm)/cm$^2$ or less, or about 0.3 (N×cm)/cm$^2$ or less. Said amounts may be suitably combined to define a range of amounts that may be used. For example, said peel strength may be from about 0.1 to 1 (N×cm)/cm$^2$, from about 0.15 to 0.3, from about 0.3 to 0.8 (N×cm)/cm$^2$, or from about 0.3 to 0.5 (N×cm)/cm$^2$ The body fluid test arrangement is provided with a fastening means of a kind that allows for a peelable connection between the body fluid test arrangement and the top sheet, and thereby for a releasable attachment of the body fluid test arrangement to the topsheet and the material thereof. The fastening means may be a mechanical fastener or an adhesive providing the peel strength properties of the arrangement.

As used herein, the term mechanical fastener refers to a fastener that mechanically engages with the surface structure of the garment to which the fastener is intended to be secured. Most preferred, the "mechanical fastener" may be a "touch fastener" providing releasable attachment to the garment. The term "touch fastener" here refers to a fastener material that comprises a backing material having a surface carrying protrusions in the form of hooks or the like that are capable of engaging the surface structure of the topsheet and attached thereto. Thus, the mechanical fastener may be a "hook-and-loop fastener" which refers to complementary fastening means having a "hook" portion and a "loop" portion and which are refastenable.

The term "hook" as used herein refers to any element capable of engaging another element, the so called "loop" portion. The term "hook" is not limited to only "hooks" in its ordinary sense, but encompasses any form of engaging elements, whether unidirectional or bi-directional. The term "loop" is likewise not limited to "loops" in its normal sense, but also encompasses any structure capable of engaging with a "hook" fastener. Examples of "loop" materials are fibrous structures, such as nonwoven materials. In this case, the topsheet such as a nonwoven layer provides the loop portion. Hook-fasteners may for example be available from Minnesota Mining and Manufacturing Company, St Paul, Minn. and as the material sold under the trademark VELCRO.

In one embodiment the fastening means is an adhesive.

As used herein, the term adhesive refers to an adhesive or glue provided on a surface of the body fluid arrangement for adhesively attaching the arrangement to the topsheet. The adhesive may be sprayed on said surface forming a coated layer on the surface and adhered thereto. The adhesive may also be applied on said surface by the use of a slot applicator, wherein the adhesive is slotted on the surface in, for example parallel stripes, or evenly over the surface. The skilled person will in view of this teaching appreciate the way an adhesive may be applied on said surface by use of a slotting or spraying technique as known in the art.

The use of an adhesive as fastening means allows for safe use and removal of the test arrangement as mentioned above, while providing comfort to a user. The specified peel strength secures that no or minimal adhesive residues remains on the topsheet after the arrangement has been peeled off from the topsheet.

The adhesive may be a pressure sensitive adhesive that is selected to provide said peel strength.

The pressure sensitive adhesive (PSA) is an adhesive, which forms bonds when pressure is applied to marry the adhesive with the adherend. The pressure-sensitive adhesive may be a commercially available adhesive. Examples of such commercially available adhesives for use in the applications of the present disclosure are NW 1052 and NW 1208 supplied by H.B. Fuller, LA 605 supplied by Savaré Speciality Adhesion, and product 2.01.01.05000123 supplied by Betasan.

The adhesive such as an pressure sensitive adhesive may be applied on a surface of said body fluid test arrangement in an amount of 10 to 40 gsm (grams per square meter) based on a total area of said surface that said adhesive is covering.

An adhesive that is sprayed or evenly slotted on said surface of the body fluid test arrangement may be applied in amount of about 10 gsm or more, about 12 gsm or more, or about 15 gsm or more. A sprayed adhesive may also be applied in amount of about 35 gsm or less, about 25 gsm or less, about 20 gsm or less or about 15 gsm or less. Said amounts may be suitably combined to define a range of amounts that may be used. For example, the applied amount may be about from 10 to 35 gsm or from about 12 to 15 gsm.

An adhesive that is slotted in parallel stripes of, for example, 10 mm in width, the stripes being spaced apart with 10 mm, may applied in an amount of about 20 gsm or more, about 25 gsm or more, about 26 gsm or more as well as about 40 gsm or less, about 30 gsm or less, or about 25 gsm or less. Said amounts may be suitably combined to define a range of amounts that may be used. For example, the applied amount may be from about 20 to 25 gsm or from about 26 to 30 gsm.

Prior to use of the body fluid test arrangement, the adhesive surface for attachment to the topsheet is conventionally covered by a release protective layer. The release protective layer acts to protect the adhesive from dirt and damage and to prevent the adhesive from adhering before the test arrangement is used.

The body fluid test arrangement may comprise a support sheet having one wearer-facing side and one fastener side on which said fastening means is arranged for the peelable connection to the topsheet.

As used herein, a wearer-facing side or surface refers to the side or surface that is intended to be directed towards the user during use.

The support sheet may be a liquid permeable sheet that preferably is of a fiber material being any one of the materials that may be used as the topsheet material described herein above. For example, the support sheet may be of a nonwoven material.

According to one embodiment, the fastening means may be an adhesive that is coated on said fastener side and thereby forms an adhesive layer on the said fastener side.

In one embodiment, the body fluid test device may be arranged on the fastener side and be in fluid communication with said support sheet and the wearer-facing side thereof.

The fluid communication provides that a fluid such as urine excreted by a wearer in contact with the body fluid test arrangement flows to the body fluid test device via the said support sheet and the wearer-facing side thereof. This arrangement allows that the body fluid test device largely is separated from the wearer-facing side by placing it on the fastener side of the support sheet. This provides a functional test arrangement that is comfortable to a wearer, while there is no or little risk that the body fluid device is damaged during use. Thus, there is provided safety during use of the body fluid test arrangement.

As mentioned hereinabove, the body fluid test device may comprise an indicator or a sensor for determining a property or constituent in body fluids, said indicator or sensor being in fluid communication with said liquid permeable layer.

In one embodiment, the body fluid test device may be a device for detecting and/or determining a developing or existing pathogen infection, preferably a UTI as is further described herein.

In one embodiment, the topsheet may comprise a fiber material. The topsheet may be of a nonwoven material, such as a spun-bond nonwoven material.

According to one aspect, there is provided an absorbent article having a longitudinal direction (y) and a transverse direction (x), side edges extending in the longitudinal direction (y) and end edges extending in the transverse direction (x) and comprising a topsheet, a backsheet and an absorbent core enclosed between said topsheet and said backsheet. The absorbent article further comprises a body fluid test arrangement according to the disclosure, wherein said arrangement is releasably attached to the topsheet of the absorbent article.

The backsheet forms a back cover of the absorbent article and will be discussed in more detail hereinbelow.

The absorbent core is the absorbent structure disposed between the backsheet and the topsheet of the absorbent article in at least a crotch region thereof. The absorbent core will be discussed in more detail in the following detailed description hereinbelow.

The disclosure will now be described in more detail with reference to embodiments and figures.

DETAILED DESCRIPTION OF EMBODIMENTS

The present disclosure relates to a body fluid test arrangement being in the form of insert for an absorbent article such as an absorbent garment. The insert is arranged with a fastening means for releasably attaching the insert to a wearer-facing side of a topsheet of the absorbent article. Thus, the insert is intended for being worn together with the absorbent article. Furthermore, the insert comprises a sensor or an indicator for collecting and/or determining body exudates properties and/or constituents.

In the following, the insert will be exemplified by a body fluid test arrangement for receiving and examining body fluids such as voided urine, wherein the arrangement is in the form of an insert of the mentioned type and comprises a body fluid test device. This body fluid test arrangement resembles to a large extent the device disclosed in DE 20 2007 005 962 U1. The device disclosed therein is meant to be used for detecting uncontrolled discharged body fluids, especially urine.

Figure 1:
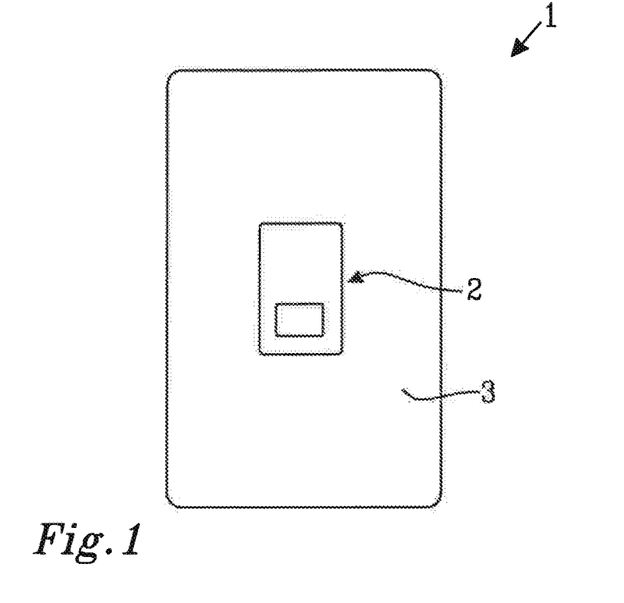
FIG. 1 is a schematic plan view of an embodiment of a body fluid test arrangement according to the disclosure. The view shows the side, which will be facing an absorbent article when the arrangement is attached thereto.

FIG. 1 illustrated such a body fluid test arrangement for detecting a voided body fluid such as urine.

Figure 2:
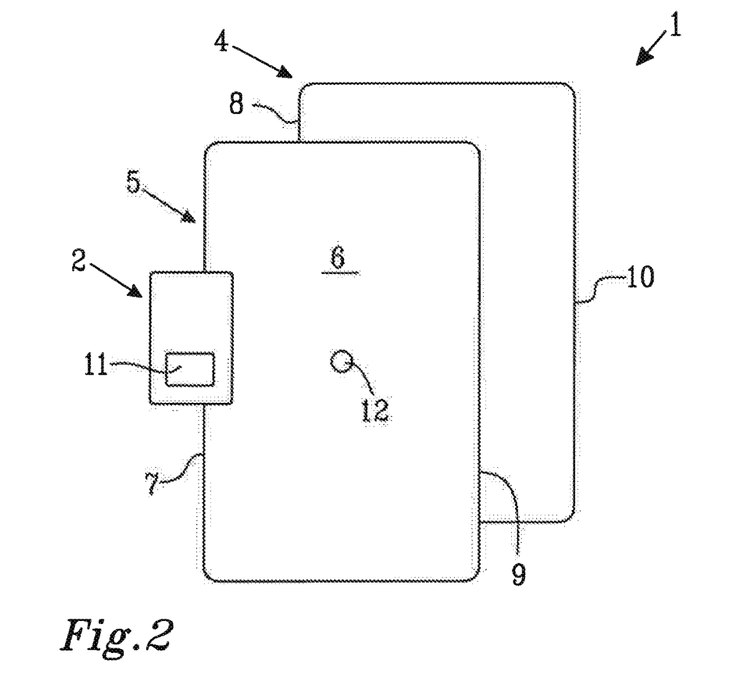
FIG. 2 is an exploded perspective view of the components of the arrangement shown in FIG. 1.

FIG. 2 is an exploded perspective view of the components of the arrangement shown in FIG. 1.

The body fluid test arrangement 1 is intended for collecting discharged body fluids, such as urine, and determining properties related thereto and/or constituents therein. The body fluid test arrangement 1 is provided with a body fluid test device 2 for determining said properties and/or constituents. The arrangement 1 may be used for detecting uncontrollably discharged urine, for example. The arrangement 1 may also be arranged for testing urine for developing and existing pathogen infections, which, for example, correspond to pH, nitrite, leukocyte and electrolyte values in the urine. Thus, a urinary tract infection may be detected and/or determined using the test arrangement.

The body fluid test arrangement 1 comprises a substantially flat rectangular body 3 which is composed of several layers, as is shown in FIG. 2. A first layer 4 is a liquid-gathering layer 4, which may be a nonwoven layer of a liquid-permeable fibrous material. The liquid-gathering layer material may be made of the materials that may also be used for the topsheet of an absorbent article as described herein above. This liquid-gathering layer 4 is meant to be placed adjacent the wearer during use and allows for excreted urine to be gathered in the body fluid test arrangement, while the test arrangement 1 is comfortable to a wearer in contact therewith.

The body fluid test arrangement 1 further comprises a second layer 5 that is a substantially flat layer having substantially the same rectangular shape and size as the liquid-gathering layer 4 to which the second layer 5 is connected. The second layer 5 may be of the same material as the first layer 4 and is provided with a fastening means 6 such as an adhesive or a mechanical fastener on one of its main sides. Thus, the second layer 5 serves as a support sheet 5 for the fastening means 6. In the following, the fastening means 6 will be further explained by reference to the use of an adhesive coating. Said adhesive coating forms an adhesive surface 6 on said main side.

An opposite side to said main side of the second layer 5 is connected to the liquid-gathering layer 4 by at least attaching the layers 4,5 to each other at and along the longitudinal edges 7, 8, 9,10 of the layers 4,5. The attachment may be provided by welding the layers 4,5 together along said edges 7, 8, 9,10. Further attachment points may be provided, such as attaching the central portions of both layers 4,5 to each other. This provides that the layers 4,5 and other components such as the body fluid test device 2 are kept in place during use, while the function of the test arrangement 1 is kept intact for collecting body fluids and detecting and/or determining properties or constituents therein.

The body fluid test device 2 in the form of a test card 2 is attached to the surface of the second layer 5 at the center thereof. The test device 2 may be a test card of the kind that is described in EP 1150609 B1. Thus, the test card 2 may comprise a test housing inside which test indicators are arranged in an indicator area 11 that may be viewed from the outside of the test card, when looking towards the side of the second layer 5 to which the test card 2 is attached. For the purpose of providing a window through which the indicator area 11 may be viewed, the test card and the housing thereof may comprise a transparent polymeric film.

The test card 2 is also provided with a fluid port that is facing the central portion of the second layer 5 and a central opening 12 thereof. The fluid port is not shown in the figures, but such a fluid port as well as the opening 12 may be arranged as is shown for the device described in EP 1150609 B1 and DE 20 2007 005 962 U1. The fluid port provides fluid contact with the central opening 12 of the second layer 5, and thereby with the liquid gathering layer 4. Voided body fluids such as urine may therefore be guided from the liquid gathering layer 4 into the test device 2 via the central opening 12 and the fluid port. Close to the fluid port inside the test card 2, a liquid swelling material may be arranged for closing the fluid port, when a sufficient amount of liquid has been collected inside the test card 2 for proper body fluid determination. Reference is made to EP 1150609 B1 and DE 20 2007 005 962 U1 for further details concerning the test card and the test arrangement related thereto.

Furthermore, a protective film for the adhesive coating may also be used (not shown). Such a protective film is releasably attached to the outer-facing adhesive surface 6 of the body fluid test arrangement 1, before or after the test arrangement 1 is in use. Such protective films for covering adhesives are well-known in the art.

In addition, the test arrangement 1 may prior to use thereof be stored in a packaging such as a cover or bag (not shown). When using the test arrangement 1, the packaging is opened and the protective film is removed from the adhesive surface and the test arrangement 1 is placed in an absorbent article such as an absorbent garment with the adhesive surface facing the wearer facing side of a topsheet of the absorbent article and adhering the test arrangement to the topsheet within a region to which excreted body fluids to be detected such as urine may be present when the absorbent article is worn by a wearer.

Figure 3A:
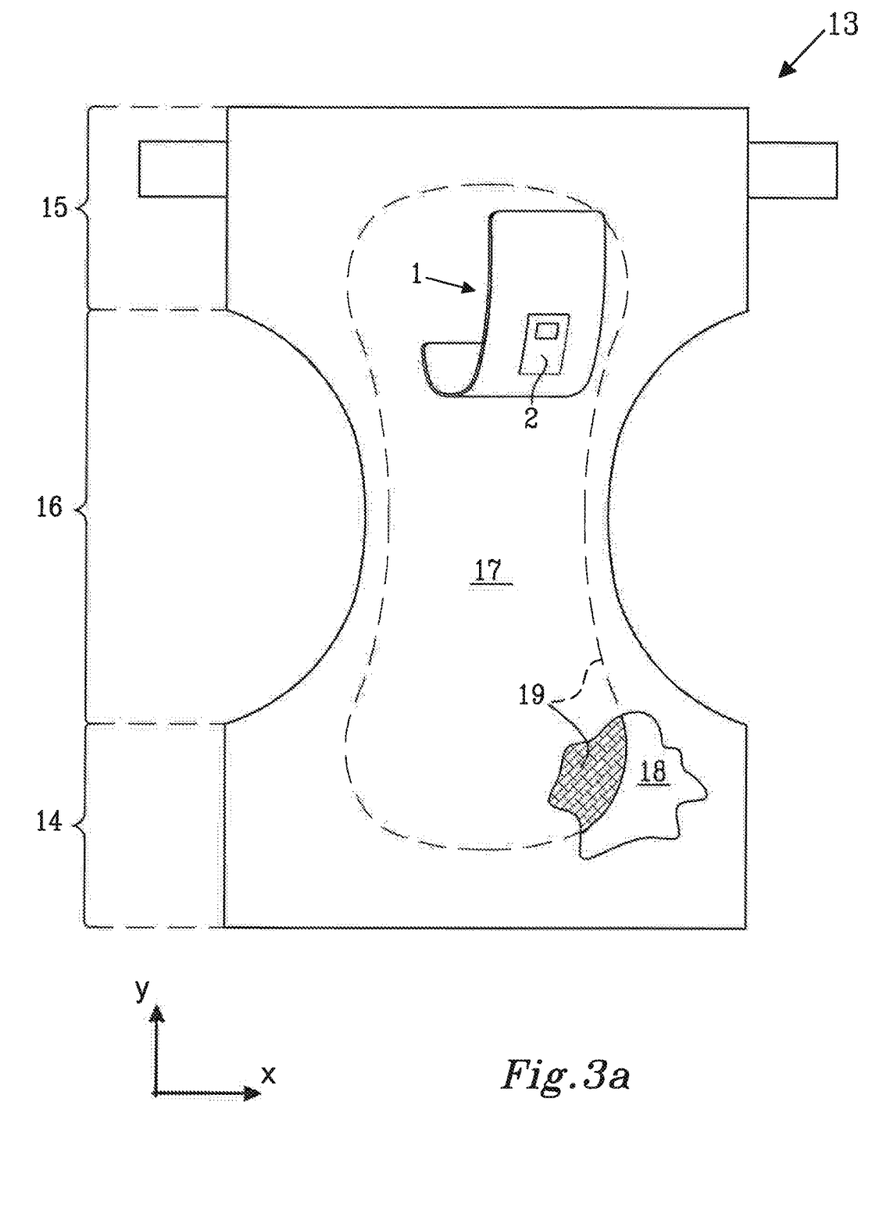
FIGS. 3a-b illustrate an ordinary absorbent garment inside which a body fluid test arrangement according to the disclosure is attached.
Figure 3B:
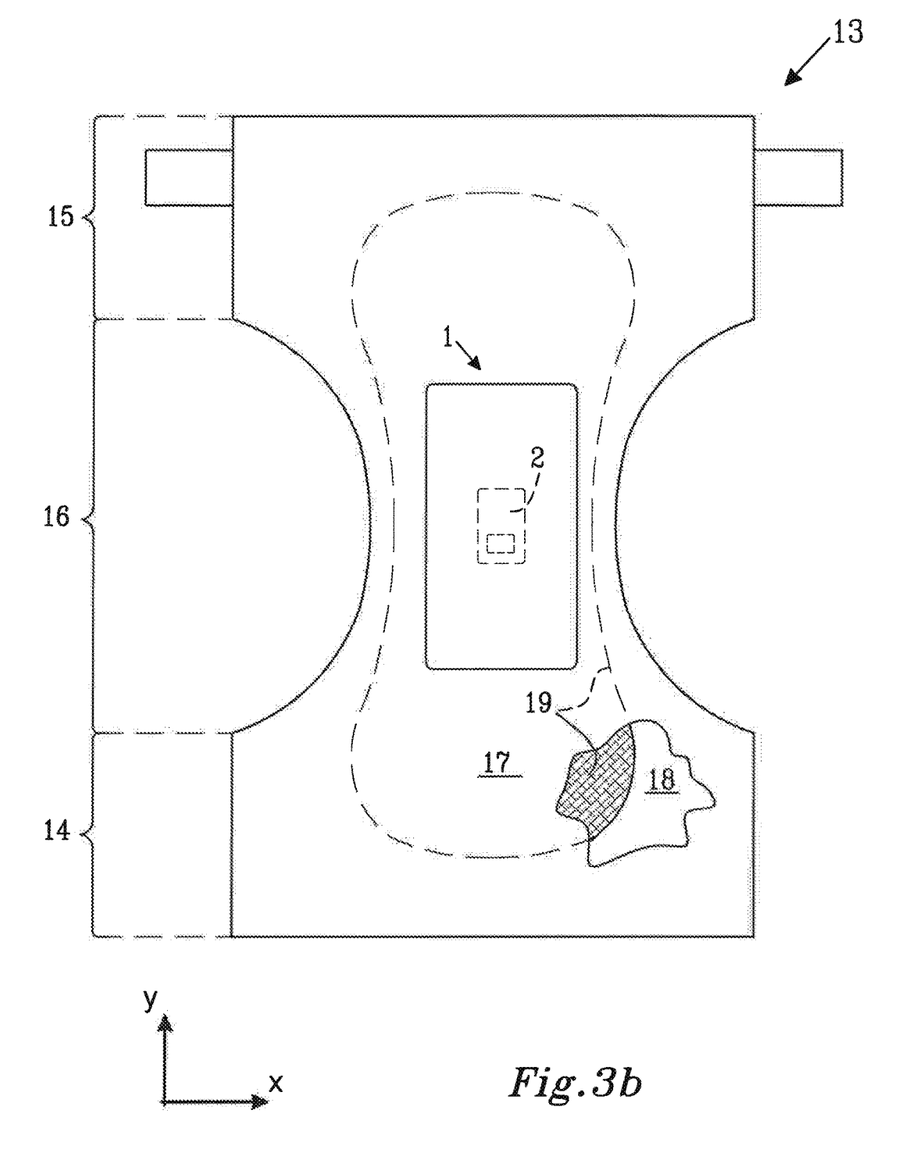

FIGS. 3a-b illustrate an absorbent garment 13 in the form of a diaper or incontinence guard to which the test arrangement 1 is attached.

The absorbent garment 13 has a longitudinal direction (y) and a transverse direction (x), and a front end portion 14, a rear end portion 15 and a crotch portion 16 located intermediate the end portions 14,15. The crotch portion 16 is the portion of the absorbent garment 13 which is intended to be placed against the crotch of a wearer during wearing of the garment 13 and to constitute the main acquisition area for body fluid that reaches the garment 13.

The absorbent garment comprises a topsheet 17, a backsheet 18 and an absorbent core 19 that is enclosed between the topsheet 17 and the backsheet 18.

The topsheet 17 refers a sheet or the like that forms the inner cover of the absorbent garment 13 and in use is placed in direct contact with the skin of the wearer. The topsheet 17 material may be any one of the materials described herein above for use in a topsheet. The material may, for example, be a nonwoven material, such as a spun-bond nonwoven.

The backsheet 18 forms the back cover of the absorbent article. The backsheet 18 may be a liquid impermeable cover 18 that may comprise a thin plastic film, e.g. a polyethylene or polypropylene film, a nonwoven material coated with a liquid impervious material, a hydrophobic nonwoven material, which resists liquid penetration, or a laminate, e.g. of a plastic film and a nonwoven material. The outer liquid impermeable cover material may be breathable so as to allow vapor to escape from the absorbent core, while still preventing liquids from passing through. Examples of breathable outer liquid impermeable cover materials are porous polymeric films, nonwoven laminates from spun-bond and meltblown layers, laminates from porous polymeric films and nonwoven materials. The backsheet may also be different in different parts of the absorbent garment.

The absorbent core 19 is the absorbent structure disposed between the topsheet 17 and backsheet 18 of the absorbent garment 13 in at least the crotch portion 16 thereof. The absorbent core 19 may be made up of any suitable absorbent or fluid uptake material as known in the art, such as one or more layers of cellulose fluff pulp, foam, fiber waddings, etc. The absorbent core 19 may contain fibers or particles of highly absorbent polymer material, commonly known as superabsorbents, which are materials having the ability to absorb and retain large quantities of fluid upon formation of a hydrogel. Superabsorbent polymers are water-swellable, water-insoluble organic or inorganic materials capable of absorbing at least about 20 times its weight of an aqueous solution containing 0.9 weight percent of sodium chloride. The superabsorbents may be mixed with cellulose fluff pulp and/or may be arranged in pockets or layers in the absorbent core 19. The absorbent core 19 may further incorporate components for improving the properties of the absorbent core 19. Some examples of such components are binder fibers, fluid-dispersing materials, fluid acquisition materials, etc. as known in the art.

The absorbent garment 13 may comprise more than one absorbent core 18. The cores may be an upper large core and a lower, small core.

The absorbent garment 13 with the body fluid test arrangement 1 attached thereto is worn as normal by a wearer, wherein the liquid gathering layer 4 of the test arrangement 1 comes in contact with the wearer and matches an area of the absorbent article 13 that may come in contact with discharged body fluids of interest, in turn providing the possibility of collecting said body fluids into the test card 2. Thus, the test arrangement 1 may be placed close to the crotch portion 16 of the absorbent garment 13.

The test card 2 is covered by the layers 4, 5 of the test arrangement 1 on one side of the test card 2 and by the topsheet 17 of the absorbent article 13 on the opposite side of the test card 2, when the test arrangement 1 is attached to the absorbent article 13, so that it is not readily visible by a viewer. This arrangement safeguards a comfort to a wearer and a functionality of the body fluid test arrangement 1. It is therefore necessary to remove the test arrangement 1 from the topsheet 17 in order to detect and/or determine properties and/or constituents of the body fluids. The test arrangement 1 should therefore be releasably attached to the absorbent garment 13.

Thus, the test arrangement 1 with collected body fluids must be peeled off from the topsheet 18 and subsequently evaluated for properties and/or constituents.

The fastening means 6 are of importance for securing the attachment of the test arrangement 1 in the absorbent article 13 during use of the absorbent article as well as providing a safe removal of the test arrangement 1 after use. A safe securement of the attachment, when the absorbent article 13 is worn, as well as a safe removal of test arrangement 1 provides that the topsheet 17 is minimally disrupted during the removal, and that the test arrangement 1 and the test device 2 therein is kept intact during use of the absorbent article 13 and the removal of the test arrangement 1 from the absorbent article 13. It is also assured that the test arrangement 1 stays in place in the absorbent article 13, where it is intended to be arranged, in order to secure an accurate measurement or indication by the body fluid test device 2 as well as to minimize any risk of disrupting said body fluid test device 2.

A safe use and removal of the test arrangement 1 is achieved by a body fluid test arrangement 1 with a fastening means that provides a releasable attachment to a topsheet material by a peelable connection there between, wherein the fastening means provides an attachment of the arrangement that has a peel strength of from 0.05 to 1.65 (N×cm)/cm$^2$ as measured according to the peel test method as described hereinbelow. Suitable peel strengths are also discussed hereinbelow in the Example section.

As mentioned hereinabove, the fastening means 6 may be an adhesive. The adhesive may be a pressure sensitive adhesive that is selected to provide peel strength values. Examples of adhesives in the present application are NW 1052 and NW 1208 supplied by H.B. Fuller, LA 605 supplied by Savaré Speciality Adhesion, and product 2.01.01.05000123 supplied by Betasan.

The use of the adhesive as fastening means 6 provides the possibility of a safe use and removal of the test arrangement 1 as mentioned above, while being providing comfort to a user.

The adhesive may be applied in an amount of an amount of about 10 to 40 gsm (grams per square meter) based on a total area the surface that said adhesive is covering. An adhesive that is sprayed or slotted on a surface of the body fluid test arrangement may be applied in amount as mentioned hereinabove.

As the skilled person will appreciate, many embodiments and alternatives are possible within the scope of the present disclosure. For example, the body fluid test arrangement 1 may be arranged with other types of body fluid test devices than the ones exemplified herein above. For example, the body fluid test device may be a wetting sensor such a color indicator or a sensor providing an electrical signal or the like as is known in the art. Furthermore, the body fluid test arrangement may be arranged with one single layer forming both the support sheet 5 and the liquid gathering layer 4, wherein a simple and safe arrangement is provided. As will also be appreciated, there may be arranged more than two layers.

Examples and Description of Test Methods

A body fluid test arrangement according to the disclosure with fastening means in the form of an adhesive were investigated for properties that provide safe use and removal of a body fluid test arrangement according to the disclosure from an absorbent article. It was found that a peel strength as measured in the peel test method as described hereinbelow may be used for testing whether or not a body fluid test arrangement provides a proper peelable connection between a body fluid test arrangement and a topsheet of an absorbent article.

The method is simple to use and only requires a reference test material in the form of a standardized fibrous material for simulating a topsheet of an absorbent article. The results from the test allow for predicting the attachment of the body fluid test arrangement to other types of topsheet materials that are normally used in an absorbent article. A test example is provided, wherein there is provided a measured peel strength that does not or minimally disrupt a topsheet as well as leaving no or little residues of adhesive on the topsheet, when the arrangement is peeled off from the topsheet. There are also indications of even more preferred peel strength values that the adhesive may have.

Peel Test Method

This test is used for determining suitable attachment strengths for a body fluid test arrangement. The test follows the general outline of ISO 11339:2010 Adhesives—T-peel test for flexible-to-flexible bonded assemblies. To accommodate the varying sizes, geometries, adhesive configurations and three-dimensional shapes that are found in different body fluid test arrangements, such as UTI test arrangement, the ISO standard has been modified in many respects.

Apparatus, Materials and Conditions

Tensile tester: Suitable apparatus and software is available e.g. from the Instron Corporation or Lloyd Instruments. The tensile tester has a fixed bottom clamp, and a movable upper clamp positioned 30 mm directly above. Both clamps should be at least 50 mm wide.

Standardized fibrous material simulating an absorbent garment topsheet is used in the method. This material is a Nylon cloth with designation Style 304, from Testfabrics, Inc., Pennsylvania. The cloth is further designated Filament Nylon 6 Tricot-Bright, and has a basis weight of 73 g/m$^2$. The cloth is oriented. When testing, the less extendible direction is aligned with the direction of pull.

Laboratory should be conditioned to 23° C. and 50% Relative Humidity.

Vacuum suction box is used for uniform pressure application on uneven topographies. A flexible rubber sheet presses the test sample against a perforated steel plate. The holes in the steel plate have a 5 mm diameter, and are centered 10 mm apart. A manometer monitors the pressure.

Procedure

Remove the body fluid test arrangement such as UTI test arrangement from its bag or casing, but leave any release paper that directly protects the adhesive agent. Condition the body fluid test arrangement and the nylon cloth in the laboratory for at least 24 hours.

Immediately before testing, remove any release paper from the body fluid test arrangement. Place the body fluid test arrangement against the nylon cloth. The cloth has been cut to the minimal rectangular shape that covers the outline of the sensor. However let the nylon cloth extend an extra 40 mm from one side of the body fluid test arrangement, where the direction of pull will be positioned in the following step.

Place the body fluid test arrangement and cloth assembly in the vacuum suction box. The cloth shall face downwards, towards the perforated steel plate. Confirm that the cloth and the body fluid test arrangement are well aligned, and that the assembly has no wrinkles. Then apply a pressure of 5 kPa for duration of 2 minutes.

Remove the assembly from the vacuum box, and let the sample rest for nine minutes. Then attach the sample into the tensile tester. The test shall start ten minutes after removal from the vacuum box.

If the body fluid test arrangement has a handle or guide for a preferred direction of removal, then center the clamp over this handle/guide. If there is no guide, then test the body fluid test arrangement from eight different directions. The directions should be spaced 45° apart, and point towards the body fluid test arrangement midpoint. In this case the adhesion equals the mean for the eight directions.

In case there is no handle, a minimal piece of the eight sheets must be detached from the nylon cloth so that it can be fastened into the clamp. The detachment should be the smallest possible that yet allows a firm fixation, and it must not significantly distort the adhesive configuration. If this cannot be done, extend the body fluid test arrangement sheet by a piece of tape or by stitching an extra piece of web, so that the clamp can get a proper hold.

Fasten the nylon cloth in the upper movable clamp, and the body fluid test arrangement in the lower (fixed) clamp. As mentioned, the clamps are 30 mm apart. The assembly should be attached without slack or excessive tension. Tare (zero) away the weight of the assembly before testing, if it unduly interferes with the results.

Start the tensile tester. The upper clamp shall move with a speed of 100 mm/minute. Stop the test when the last adhesion element lets go from the cloth. Read the total energy required for removal. This equals the integrated area under the curve depicting force versus displacement, as expressed in N×cm (force in Newton multiplied with the separation distance in cm). To put the integrated force in relation to the body fluid test arrangement sheet's size, divide the integrated force with the area of the whole sheet (i.e. the area circumscribed by the outer boundaries of the sheet, including any handle). The relevant adhesion unit in the context of this disclosure will then be ((N×cm)/cm$^2$).

EXAMPLE

A body fluid test arrangement being a UTI sensor arrangement in the form as described hereinabove with reference to the figures was provided with a pressure sensitive adhesive, being an adhesive available from Betasan as product 2.01.01.05000123, on the support sheet thereof in an amount of about 35 gsm based on a total area of an surface that said adhesive is covering. The adhesive was slotted evenly on a support sheet surface of the UTI sensor arrangement. The UTI sensor arrangement had a support sheet with a length of 15 cm, along which 14 cm has an adhesive for attachment to a topsheet and 1 cm at one end forms grip and handle area for a user to grip. The support sheet and the adhesive thereon had a width of 8 cm. The UTI sensor arranged in the center of the support sheet had a length of 5 cm and a width of 3.5 cm. It is appreciated that the area covered by the UTI sensor device is not carrying any adhesive for attachment to the topsheet. The UTI sensor arrangement was tested according to the peel test method hereinabove.

The peel test resulted in a measured peel strength of 1.37 (N×cm)/cm$^2$. No or minimal residues of adhesive were remaining on a topsheet after the arrangement has been peeled off from the topsheet. There was also no or little disruption of the topsheet. This indicates an adhesive provided test arrangement that is suitable for use in the attachment to a topsheet of an absorbent garment.

Furthermore, there are indications that a peel strength as low as about 0.05 (N×cm)/cm$^2$ would provide a suitable attachment. Nevertheless, in order to provide a proper securing of the arrangement in an absorbent article during use thereof, it is indicated that a peel strength of about 0.08 (N×cm)/cm$^2$ or more, about 0.1 (N×cm)/cm$^2$ or more, about 0.15 (N×cm)/cm$^2$ or more, about 0.30 (N×cm)/cm$^2$ or more or about 0.5 (N×cm)/cm$^2$ or more may be used.

There are also indications that an body fluid test arrangement providing a peel strength of up to about 1.65 (N×cm)/cm$^2$ may be suitable in the aspects of not disrupting the topsheet or leaving any residues of adhesive on the topsheet, when the test arrangement is peeled off from a topsheet. Nevertheless, the peel strength may be about 1.4 (N×cm)/cm$^2$ or less, about 1.3 (N×cm)/cm$^2$ or less, about 1.0 (N×cm)/cm$^2$ or less, about 0.8 (N×cm)/cm$^2$ or less, about 0.5 (N×cm)/cm$^2$ or less, or about 0.3 (N×cm)/cm$^2$ or less.

A good securing of a body fluid test arrangement, while there is substantially no risk of disrupting the topsheet when the test arrangement is peeled off from the topsheet, may, for example, be provided, when there is a peel strength from about 0.1 to 1 (N×cm)/cm$^2$, from about 0.15 to 0.3, or from about 0.3 to 0.8 (N×cm)/cm$^2$ the applied as measured according to the peel test method herein above.

The invention claimed is:

1. A body fluid test arrangement for an absorbent article, wherein the body fluid test arrangement comprises a body fluid test device for receiving and examining voided body fluid, said body fluid test arrangement being configured to attach to a topsheet of the absorbent article, wherein said body fluid test arrangement comprises a fastener for attachment to the topsheet of the absorbent article by a peelable connection between the body fluid test arrangement and the topsheet, wherein the fastener provides an attachment of the body fluid test arrangement having a peel strength from 0.05 to 1.65 (N×cm)/cm$^2$ as measured according to the peel test method as described in the specification, wherein the fastener is an adhesive that is applied on a surface of said body fluid test arrangement in an amount of 10 to 40 gsm based on a total area of said surface that said adhesive is covering, wherein the body fluid test arrangement comprises a support sheet having one wearer-facing side and one fastener side on which said fastener is arranged for the attachment to the topsheet, and the body fluid test device is arranged on said fastener side and is in fluid communication with said wearer-facing side of said support sheet.

2. The body fluid test arrangement according to claim 1, wherein the adhesive is a pressure sensitive adhesive.

3. The body fluid test arrangement according to claim 1, wherein the support sheet is a liquid permeable sheet.

4. The body fluid test arrangement according to claim 1, wherein the fastener is an adhesive that is coated on said fastener side and forms an adhesive layer on said fastener side.

5. The body fluid test arrangement according to claim 1, wherein said peel strength is from 0.05 to 1.4 $(N \times cm)/cm^2$.

6. The body fluid test arrangement according to claim 1, wherein the body fluid test device is a device for detecting and/or determining a developing or existing pathogen infection.

7. The body fluid test arrangement according to claim 6, wherein the pathogen infection is a urinary tract infection.

8. The body fluid test arrangement according to claim 1, wherein the topsheet comprises a fiber material.

9. An absorbent article comprising a topsheet, a backsheet and an absorbent core enclosed between said topsheet and said backsheet, wherein the absorbent article further comprises a body fluid test arrangement according to claim 1, wherein said body fluid test arrangement is releasably attached to the topsheet of the absorbent article.

10. The body fluid test arrangement according to claim 1, wherein the support sheet is a liquid permeable sheet of a fiber material.

11. The body fluid test arrangement according to claim 10, wherein the fiber material comprises a nonwoven fiber material.

12. The body fluid test arrangement according to claim 1, wherein the peel strength is from 0.1 to 1 $(N \times cm)/cm^2$.

13. The body fluid test arrangement according to claim 1, wherein the peel strength is from 0.15 to 0.8 $(N \times cm)/cm^2$.

14. The body fluid test arrangement according to claim 1, wherein the peel strength is from 0.3 to 0.5 $(N \times cm)/cm^2$.

15. The body fluid test arrangement according to claim 1, wherein the topsheet comprises a nonwoven fiber material.

* * * * *